(12) United States Patent
Muta et al.

(10) Patent No.: US 6,432,431 B1
(45) Date of Patent: Aug. 13, 2002

(54) STEROID-CONTAINING CATAPLASMS AND PROCESS FOR PRODUCING THE SAME

(75) Inventors: Kazunori Muta; Seiichiro Tsuru; Taro Yamahata, all of Tosu (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/743,459

(22) PCT Filed: Jul. 7, 1999

(86) PCT No.: PCT/JP99/03673

§ 371 (c)(1),
(2), (4) Date: Jan. 10, 2001

(87) PCT Pub. No.: WO00/02563

PCT Pub. Date: Jan. 20, 2000

(30) Foreign Application Priority Data

Jul. 10, 1998 (JP) ............................................. 10-195933

(51) Int. Cl.[7] ........................ A01N 25/34; A01N 25/00; A61F 13/00; A61K 9/70; A61K 9/14
(52) U.S. Cl. ........................ 424/402; 424/401; 424/405; 424/443; 424/449; 424/484; 424/486
(58) Field of Search ................................ 424/401, 402, 424/443, 449, 405, 484, 486

(56) References Cited

U.S. PATENT DOCUMENTS 4,008,321 A * 2/1977 Kamishita et al. .......... 424/243
4,244,942 A * 1/1981 Kamishita et al. ............ 424/81

FOREIGN PATENT DOCUMENTS

| JP | 63-51330 | 3/1988 |
| JP | 63-201119 | 8/1988 |
| JP | 5-271077 | 10/1993 |
| JP | 6-271468 | 9/1994 |
| JP | 7-188027 | 7/1995 |
| JP | 8-53354 | 2/1996 |

* cited by examiner

Primary Examiner—Thurman K. Page
Assistant Examiner—Humera N. Sheikh
(74) Attorney, Agent, or Firm—Fitch, Even, Tabin & Flannery

(57) ABSTRACT

A steroid-containing gel patch containing a steroid as an effective ingredient at 0.005 to 0.05% by weight, crotamiton as a stabilizer at 15% by weight or less and a surfactant in a base, where the amount of the crotamiton blended being 200 to 3000-fold the weight of the steroid blended and the amount of the surfactant blended being $\frac{1}{20}$ to $\frac{1}{5}$-fold the weight of the crotamiton blended.

13 Claims, No Drawings

STEROID-CONTAINING CATAPLASMS AND PROCESS FOR PRODUCING THE SAME

This application is the national phase of international application PCT/JP99/03673 filed Jul. 7, 1999 which designated the U.S., and that international application was published under PCT Article 21(2) in English.

TECHNICAL FIELD

The present invention relates to steroid-containing gel patches (cataplasms) and a process for producing the same; more specifically, the present invention relates to steroid-containing gel patches comprising crotamiton as a stabilizer and a surfactant and being stable over time, and a process for producing the same.

BACKGROUND ART

Adrenal cortex hormones (steroids) and the like have conventionally been used as principal drugs for allergic dermal diseases such as eczema, the dermatitis group, psoriasis, prurigo, erythema, insect bite, chronic discoid lupus erythematosus, asialoid lichen, lichen ruber planus, and atopic dermatitis. Sticking dosage forms described in Japanese Patent Laid-open Nos. 51330/1988 and 53354/1996 have been known to contain such steroids as effective ingredients.

The sticking dosage form described in Japanese Patent Laid-open No. 51330/1988 is prepared by blending steroids in an adhesive gel base containing a water-soluble polymer, water and a water-retentive agent as essential ingredients. So as to increase the solubility and dispersibility of steroids in water, described in Japanese Patent Laid-Open No. 51330/1988 is blending of oil components such as crotamiton, benzyl alcohol, isopropyl myristate, ethylene glycol, diethyl sebacate, and 2-ethyl-5-pyrrolidone as well as surfactants. The sticking dosage form described in Japanese Patent Laid-open No. 53354/1996, of which the inventors are partially overlapped with those of the present invention and the assignee is the same as the assignee of the present invention, is prepared by blending adrenal cortex hormones in base components comprising a water-soluble polymer, a moisturizer, water, a dissolution agent and/or an absorption promoting agent; and the dissolution agent or absorption promoting agent includes oleic acid, glycol salicylate, benzyl alcohol, isopropylmyristate, crotamiton, oleyl alcohol, mint oil, eucalyptus oil, limonene, isopulegol, 3-1-menthoxypropan-1,2-diol, or other essential oils or surfactants.

DISCLOSURE OF THE INVENTION

When such conventional sticking dosage forms are applied to so-called gel patches with a relatively high water content in the bases, however, steroids at their dissolution state are rapidly hydrolyzed; and additionally, the adhesive strength of the resulting gel patch is decreased over time, disadvantageously. Therefore, such conventional sticking dosage forms are not yet satisfactory from the respect of the stability of the dosage forms over time.

The present invention has been achieved in terms of the problems of the conventional techniques. It is a purpose of the present invention to provide gel patches with a remarkably excellent stability over time, where the decomposition of steroids can be sufficiently prevented despite of dissolution states of the steroids. In the gel patches described above, the adhesive strength is stable over time and neither so-called bleeding due to phase separation in the base nor so-called stickiness due to the decrease of the adhesive force of the base occurs. It is also an object of the present invention to provide a process for efficiently producing the above mentioned gel patches.

The present inventors have made investigations so as to attain the purpose. Consequently, the inventors have found that a gel patch containing steroids as effective ingredients can comply with the purpose even at dissolution state, when the gel patch is blended with a considerably larger volume of crotamiton as being a stabilizer compared to that employed in conventional sticking dosage forms, and with a surfactant having its predetermined blend ratio to crotamiton. Thus, the present invention has been achieved.

The gel patch (cataplasm) of the present invention is a steroid-containing gel patch containing a steroid at 0.005 to 0.05% by weight (abbreviated as wt % hereinbelow), crotamiton below 15 wt % as a stabilizer and a surfactant, as the effective ingredients in the base, wherein the amount of the crotamiton blended is 200- to 3000-fold the weight of the steroid blended and the amount of the surfactant blended is $1/20$- to $1/5$-fold the weight of the crotamiton blended.

The process for producing the gel patch in accordance with the present invention comprises a step of mixing 0.005 to 0.05 part by weight of the steroid with crotamiton at an amount 200- to 3000-fold the weight of the steroid and at 15 parts by weight or less, to recover a solution of the steroid in crotamiton, a step of mixing together a surfactant at an amount $1/20$- to $1/5$-fold the weight of crotamiton, water, a water-soluble polymer, and a moisturizer to recover a homogeneous kneaded mixture, and a step of adding the solution of the steroid in crotamiton to the kneaded mixture to recover a gel patch in which the steroid is homogeneously dispersed at dissolution state.

BEST MODE FOR CARRYING OUT THE INVENTION

The steroid-containing gel patch of the present invention is now described in detail hereinbelow. The steroid contained as the effective ingredient in the gel patch of the present invention includes for example diflucortolone valerate, difluprednate, prednisolone acetate valerate, betametasone valerate, dexametasone valerate, beclometasone propionate, hydrocortisone propionate butyrate, diflorazone acetate, dexametasone propionate, betametasone dipropionate, fluocinolone acetonide, triamcinolone acetonide, dexametasone, methylprednisolone, prednisolone, hydrocortisone, parametasone, betametasone, sodium betametasone phosphate, dexametasone acetate, cortisone acetate, hydrocortisone acetate, fluocinonide, fluorometholone, methylprednisolone acetate, halcinonide, budesonide, and alclometasone propionate; among them, a preference is given to betametasone valerate, dexametasone valerate, prednisolone acetate valerate, beclometasone propionate and fluocinolone acetonide. Betametasone valerate is particularly preferable for gel patches intended for eczema, dermatitis and atopic dermatitis and the like.

The steroids described above are contained at 0.005 wt % to 0.05 wt %, preferably at 0.01 wt % to 0.04 wt %, more preferably at 0.01 wt % to 0.03 wt % in gel patch bases. When the steroid content is less than 0.005 wt %, sufficient pharmacological effects can be yielded with much difficulty; when the steroid content is more than 0.05 wt %, alternatively, the amount of the steroid blended in the gel patch is so excessive that the imbalance between crotamiton and the surfactant then occurs, resulting in no procured steroid stability and no stability of the dosage form.

As effective ingredients, contained in the gel patches of the present invention are crotamiton as a stabilizer and a surfactant in their predetermined amounts. As described below, the use of crotamiton at a predetermined blend ratio to steroids and a surfactant at a predetermined blend ratio to the crotamiton in combination brings about the advantages of the present invention as described below, such as sufficient stability of steroids at dissolution state over time. Alternatively, dissolution agents except for crotamiton, such as fatty acid esters including diethyl sebacate and isopropyl myristate, can never sufficiently dissolve steroids, while polyethylene glycol and benzyl alcohol and the like eventually cause inconveniences such as an occurrence of steroid crystallization in the gel patch base. Thus, such dissolution agents can never attain the stability of steroids at dissolution state over time.

It is required that the amount of crotamiton blended in the gel patch of the present invention is below 15 wt % in the base (gel patch base or cataplasm base) and is 200- to 3000-fold the weight of the steroid blended therein. Preferably, the amount of crotamiton blended in the gel patch of the present invention is below 13 wt % in the base and is 250-to 1500-fold the weight of the steroid blended therein. More preferably, the amount of crotamiton blended in the gel patch of the present invention is below 10 wt % in the base and is 300-to 1200-fold the weight of the steroid blended therein.

When the amount of crotamiton blended is below 200-fold the weight of the steroids blended, the steroid is hydrolyzed in the base over time, so that the stability of the resulting gel patch over time can never be procured. When the amount of crotamiton blended ismore than 15wt % and exceeds 3000-fold the weight of the steroid blended, disadvantages occur, including a decrease of the adhesive force of the base, a decrease of the adhesive strength, a presence of residual plaster (so-called stickiness) and crotamiton bleeding from the base.

Conventional steroid-containing sticking dosage forms described in Japanese Patent Laid-open Nos. 51330/1988 and 53354/1996 contain crotamiton as one of dissolution agents. Because of the finding that a higher amount of blended crotamiton readily causes the occurrence of inconveniences such as phase separation, the amount of crotamiton blended was about 2- to 20-fold the weight of the steroids blended. In contrast, the present inventors have found that crotamiton blended at an amount fairly above the conventional range of blended crotamiton can prevent the decomposition of steroids at dissolution state over time, quite unexpectedly from conventionally known findings and that the use of a surfactant blended at a predetermined ratio to crotamiton in combination can sufficiently prevent the occurrence of phase separation and the like. Because steroids in the base are present not at dispersed state of crystal but at dissolution state in the gel patch of the present invention, steroids are homogeneously dispersed to effectively exert their pharmacological efficacy, so that the steroids can stably retain the pharmacological efficacy at a high level even when the steroids are at the blend amount described above.

As described above, a predetermined amount of a surfactant is contained in the base of the gel patch of the present invention, so as to homogeneously emulsify and disperse crotamiton that is a hydrophobic component in the base. The amount of a surfactant blended in the gel patch of the present invention is $1/20$-fold to $1/5$-fold, preferably $1/15$-fold to $1/6$-fold, more preferably $1/12$- to $1/8$-fold the weight of crotamiton blended.

When the amount of the surfactant blended is less than $1/20$-fold the weight of crotamiton blended, sufficient homogeneity can't be attained since crotamiton is neither emulsified nor dispersed well in the base. Additionally, crotamiton is separated from the steroid phase and is then bled out of the base, disadvantageously, leading to the occurrence of so-called bleeding. Consequently, the stability of steroids at dissolution state can never be retained over time. On the other hand, when the amount of the surfactant blended is more than $1/5$-fold the weight of crotamiton blended, the adhesive force of the base is decreased, so that the plaster partially remains on the skin during stripping. Problems such as so-called stickiness and the deterioration of the adhesive strength of the base due to the storage for a prolonged period of time occur or the stability of the steroid at the dissolution state over time can never be retained.

The surfactant of the present invention is preferably a nonionic surfactant. As such nonionic surfactant, one or more surfactants may satisfactorily be used in combination. When nonionic surfactants are used, the surfactants are at great compatibility with the gel patch, so that the oily components can be dispersed well in the gel patch, which brings about great convenience for use, such as the increase of adhesion.

Preferably, the nonionic surfactant of the present invention includes polyglycerine fatty acid esters such as monooleate diglyceryl, tristearate hexaglyceryl, and pentaoleate decaglyceryl; sorbitan fatty acid esters such as monostearate sorbitan, trioleate sorbitan and sesqui-isostearate sorbitan; polyoxyethylene sorbitan fatty acid esters such as monopalmitate polyoxyethylene glycol sorbitan and monooleate polyoxyethylene glycol sorbitan; polyoxyethylene sorbit fatty acid esters such as hexastearate polyoxyethylene glycol sorbit and tetraoleate polyoxyethylene glycol sorbit; polyethylene glycol fatty acid esters such as monolaurate polyethylene glycol, monostearate polyethylene glycol and monooleate polyethylene glycol; polyoxyethylene alkyl ethers such as polyoxyethylene lauryl ether, polyoxyethylene cetyl ether and polyoxyethylene oleyl ether; polyoxyethylene alkyl phenyl ethers such as polyoxyethylene nonyl phenyl ether and polyoxyethylene octyl phenyl ether. Among them, a preference is given to monooleate diglyceryl, monostearate polyethylene glycol (2EO), sesqui-isostearate sorbitan, tristearate hexaglyceryl and polyoxyethylene (10) hardened castor oil, particularly.

The surfactant for use in the steroid-containing gel patches of the present invention is preferably at an HLB (hydrophile-lipophile-balance) value of 2 to 11, more preferably at an HLB value of 3 to 8. A surfactant at an HLB value less than 2 readily causes the phase separation of the base, which tends to deteriorate the stability of the gel patches as a dosage form and the convenience for use. The surfactant with an HLB value larger than 11 readily causes the bleeding of the compositions in the base and stickiness of the base.

The base of the gel patch of the present invention preferably contains water, a water-soluble polymer and a moisturizer in addition to the steroid as an effective ingredient, crotamiton as a stabilizer and the surfactant. The water contained in the base is preferably at 20 to 70 wt %, more preferably at 30 to 60 wt %.

Additionally, the water-soluble polymer preferably includes gelatin, agar, alginic acid, mannan, carboxymethyl cellulose, carboxymethyl cellulose sodium, methyl cellulose, methyl cellulose sodium, hydroxypropyl cellulose, hydroxypropyl cellulose sodium, polyvinyl alcohol, polyacrylic acid and polyacrylate sodium and the like, or at least one of them, which is crosslinked with an organic or inorganic crosslinking agent. Further, one or more water-soluble polymers may satisfactorily be used in combination, depending on the properties of the gel patch base. The content of the water-soluble polymer in the base is preferably 0.1 to 30 wt %, more preferably 0.5 to 15 wt %.

Furthermore, the moisturizer (emmolient) preferably includes polyhydric alcohols such as polyethylene glycol, glycerin, sorbitol, maltitol, propylene glycol, 1,3-butanediol, and reduced maltose thick malt syrup. Additionally, one or more of such moisturizers may satisfactorily be used in combination. The content of the moisturizer in the base is preferably 10 to 60 wt %, more preferably 20 to 50 wt %.

The gel patch base of the present invention may satisfactorily contain additives such as crosslinking agents for crosslinking polymers to increase the adhesive strength, fillers, preservatives, pH adjusters, antioxidants, ultraviolet absorption agents, and absorption promoting agents, within a pharmaceutically acceptable range.

Preferably, the crosslinking agents include polyvalent metal compounds such as aluminium hydroxide, calcium hydroxide, calcium chloride, aluminium sulfate, aluminium sulfate ammonium, magnesium aluminate metasilicate, synthetic aluminium silicate and dihydroxyaluminium aminoacetate; and organic compounds such as polyglycerine polyglycidyl ether, ethylene glycol diglycidyl ether, polypropylene glycol diglycidyl ether and sorbitan polyglycidyl ether. Additionally, one or more crosslinking agents may satisfactorily be used in combination. The content of the crosslinking agent in the base is preferably 0.01 to 5 wt %, more preferably 0.05 to 2 wt %.

The additives other than the various components described above include preservatives such as methylparaben, propylparaben, thymol and isopropylmethylphenol; pH adjusters such as sodium hydroxide, citric acid, acetic acid, diethanol amine and triethanol amine; antioxidants such as ascorbic acid, dibutylhydroxytoluene, gallate ester, vitamin E, vitamin E acetate ester and disodium edate; inorganic fillers such as kaolin, zinc white, titanium dioxide, talc, bentonite, and sodium hydrous silicate; ultraviolet absorption agents such as p-aminobenzoate ethyl, 2-hydroxy-4-methoxybenzophenone, and phenylsalicylate; cool components such as 1-menthol; hot components such as capsicin; stabilizers except for crotamiton and surfactants; and absorption promoting agents.

As described above, the steroid-containing gel patches of the present invention contain a predetermined amount of the steroid, crotamiton at a predetermined blend ratio to the steroid, and a surfactant at a predetermined blend ratio to crotamiton, resulting in a high-level stability over time. Such stability has never been attained by conventional gel patches containing the steroid at dissolution state. More specifically, the residual steroid ratio in the steroid-containing gel patch of the present invention is 95% or more, under storage at a relative humidity of 75% and a temperature of 60° C. for one month. Such high-level residual steroid ratio has never been attained by conventional gel patches containing the steroid at dissolution state. The high-level residual steroid ratio can be attained for the first time by the steroid-containing gel patch of the present invention. Herein, the residual steroid ratio expresses the ratio of residual steroid to the initial steroid, which is represented in the formula: [%]{=(steroid content after storage/initial steroid content)×100}. The ratio is calculated on the basis of the steroid content (initial steroid content) in the gel patch immediately after its production and that (steroid content after storage; weight basis) after storage of the gel patch sealed in an air-tight aluminum package under conditions of a relative humidity of 75% and a temperature of 60° C. for one month.

A reason why the steroid-containing gel patches of the present invention can attain the high-level stability over time is not yet elucidated, but the inventors deduce the reason as follows. More specifically, it is believed that steroid hydrolysis can be prevented by confining the steroid in a hydrophobic solvent to reduce the probability of the steroid in contact to water. The probability of the contact between the steroid molecules and water molecule can be reduced exceedingly since a larger volume of hydrophobic solvent crotamiton is present compared to the volume of the steroid in the gel patches of the present invention, making such steroid molecules present stably in aqueous bases.

The steroid-containing gel patch of the present invention further comprises a support comprising elastic woven fabric, knitted fabric, non-woven fabric and non-woven paper. Such support may preferably be at a mean air permeability of 200 $cm^3/cm^2/S$ or less as measured according to JIS L 1096-1979 6.27.1A method, more preferably within a range of 50 to 150 $cm^3/cm^2/S$. When the mean air permeability of the support is above 200 $cm^3/cm^2/S$, the adhesive base of the gel patch transfers to the side of non-woven fabric, leading to a ready occurrence of base bleeding, so that sufficient stability of the resulting dosage form is likely to be hardly procured.

Still furthermore, the support of the present invention is preferably an elastic support comprising a support portion with 50% modulus of 0.1 to 2.0 kg/5 cm and with the elongation recovery during 50% elongation being 40% or more. Because such support permits the resulting gel patch to follow vigorous motions of body parts such as joint when attached thereon and the support readily resumes the original shape even after elongation, the support can prevent the gel patches from being stripped away during use or being peeled of f. The support also can prevent the plaster from being floated. Thus, the effectiveness and applicability of the resulting gel patch can be likely to be enhanced. More specifically, when the 50% modulus of the support is less than 0.1 kg/5 cm, the strength is reduced and the conformability during plaster pasting is likely to be deteriorated; when the 50% modulus is above 2.0 kg/5 cm, peeling occurs if the plaster is at a low adhesive strength; when the adhesive strength of the plaster is high, alternatively, the lesion cramps to cause the gel patch to be readily peeled off. When the elongation recovery during 50% elongation of the support is less than 40%, the plaster floats up from skin to cause the gel patch to be readily peeled off. When the elongation recovery during 50% elongation is 40% or more, preferably 55% or more, the resulting gel patch can follow drastic skin motion with great applicability.

The steroid-containing gel patches of the present invention may further be satisfactorily provided with a stripping coating. Such stripping coating is appropriately selected from plastic films such as polyethylene, polypropylene and polyester, and stripping paper.

The process for producing the steroid-containing gel patch of the present invention is now described. First of all, the following steps are performed: step A of preparing a solution of a steroid in crotamiton by mixing 0.005 to 0.05 part by weight of the steroid with crotamiton 200- to 3000-fold the weight of the steroid and 15 parts by weight or less; and step B of preparing a homogeneous kneaded mixture by mixing a surfactant ¹⁄₂₀- to ⅕-fold the weight of the crotamiton, preferably 20 to 70 parts by weight of water, preferably 0.1 to 30parts by weight of a water-soluble polymer, preferably 10 to 60 parts by weight of a moisturizer, and a crosslinking agent and an additive if necessary. Subsequently, the solution of the steroid in crotamiton as recovered in the step A. is added to and mixed with the kneaded mixture recovered in the step B. In such manner, the gel patch (gel patch base) of the present invention where the steroid is homogeneously dispersed at dissolution state can be recovered. By directly spreading the resulting gel patch base on a support or spreading the gel patch base on a stripping coating prior to transferring the base under pressure on a support, the gel patch of the present invention (gel patch attached with support) may be produced.

According to the process, a steroid can be at a sufficient dissolution state during the preparation of the solution of the steroid in crotamiton and is thereafter kneaded and mixed with a kneaded mixture comprising other components. Hence, the steroid can be retained at a sufficiently dissolved and homogeneously dispersed state in the gel patch base. Herein, the sequence of blending various components according to the process is not limited to the blending sequence as described above, but may appropriately be modified, satisfactorily.

According to the process, the amount of the base to be coated on the support is 400 g/m$^2$ or more to 550 g/m$^2$ or less. When the amount thereof coated is above 400 g/m$^2$, the vaporization of water in the gel patch is so slow that the adhesivity can be enhanced. Accordingly, the attachment of the resulting gel patch can likely to be endured for a prolonged period of time. When the amount thereof to be coated is below 550 g/m$^2$, a gel patch with great applicability may be recovered, with less hard touch during attachment, so that it can be prevented from being peeled off due to abrasion with clothes.

EXAMPLES

The present invention will now be described in more detail, with reference to preferable examples and comparative examples and test examples in accordance with the present invention. The present invention is not limited to these examples. Herein, the term "part" means "part by weight" in the examples and comparative examples.

Example 1

49.845 parts of distilled water, 9.5 parts of kaolin, 0.25 part of titanium oxide, 0.6 part of sesqui-oleate sorbitan (HLB=4.3), 0.5part of synthetic aluminium silicate, and 0.3 part of tartaric acid were placed in a mixer; and the resulting mixture was dissolved at about 50° C. to prepare a homogenous dispersion solution. Then added to the dispersion solution were a preliminarily prepared dispersion solution of 24 parts of glycerin, 9 parts of polyacrylate sodium, and 3 parts of carboxymethyl cellulose sodium, for mixing under agitation to prepare a homogenous kneaded mixture. Mixed into the kneaded mixture was a solution of 0.005 part of betametasone valerate preliminarily dissolved in 3 parts of crotamiton, to prepare a gel patch base in which betametasone valerate was homogeneously dispersed at dissolution state. Using a spreader, then, the base was spread on a non-woven fabric (mean air permeability of 120 cm$^3$/cm$^2$/s) to 500 g/m$^2$; then, the base surface was coated with a polyester film, which was then cut into pieces of a predetermined size (7.5 cm×10.0 cm) to prepare a gel patch (product).

Example 2

36.04 parts of distilled water, 5 parts of gelatin, 3 parts of polyvinyl alcohol, 5 parts of kaolin, 0.25 part of monostearate polyethylene glycol (2EO) (HLB=4), 0.2 part of dihydroxyaluminium aminoacetate and 0.5 part of tartaric acid were placed in a mixer; and the resulting mixture was dissolved at about 50° C. to prepare a homogenous dispersion solution. Then added to the dispersion solution was a preliminarily prepared dispersion solution of 40 parts of glycerin and 5 parts of polyacrylate sodium, for mixing under agitation to prepare a homogenous kneaded mixture. Mixed into the kneaded mixture was a solution of 0.01 part of dexametasone valerate preliminarily dissolved in 5 parts of crotamiton, to prepare a gel patch base in which dexametasone valerate was homogeneously dispersed at dissolution state. In the same manner as in Example 1, then, a gel patch (product) was prepared by using this base.

Example 3

40.88 parts of distilled water, 3 parts of gelatin, 2.5 parts of polyvinyl alcohol, one part of Carbol, one part of titanium oxide, 0.5 part of monostearate sorbitan (HLB=4.7) and 0.1 part of polyethylene glycol diglycidyl ether were placed in a mixer; and the resulting mixture was dissolved at about 50° C., to prepare a homogenous dispersion solution. Then added to the dispersion solution was a preliminarily prepared dispersion solution of 30 parts of glycerin, 10 parts of polyethylene glycol and 5 parts of carboxymethyl cellulose sodium, for mixing under agitation to prepare a homogenous kneaded mixture. Mixed into the kneaded mixture was a solution of 0.02 part of prednisolone acetate valerate preliminarily dissolved in 6 parts of crotamiton, to prepare a gel patch base in which prednisolone acetate valerate was homogeneously dispersed at dissolution state. In the same manner as in Example 1, then, a gel patch (product) was prepared by using this base.

Example 4

48.985parts of distilled water, 3parts of polyvinyl alcohol, 0.5 part of carboxyvinyl polymer, 6 parts of kaolin, 0.5 part of titanium oxide, 0.375 part of monolaurate sorbitan (HLB=8.6), 14 parts of sorbitol solution (70%) and 0.3 part of tartaric acid were placed in a mixer; and the resulting mixture was dissolved at about 50° C. to prepare a homogenous dispersion solution. Then added to the dispersion solution was a preliminarily prepared dispersion solution of 15 parts of glycerin, 5 parts of sodium polyacrylate, 0.15 part of magnesium aluminate metasilicate, 0.01 part of dry aluminium hydroxide gel, and 0.15 part of sodium edetate, for mixing under agitation to prepare a homogenous kneaded mixture. Mixed into the kneaded mixture was a solution of 0.03 part of betametasone valerate preliminarily dissolved in 6 parts of crotamiton, to prepare a gel patch base in which betametasone valerate was homogeneously dispersed at dissolution state. In the same manner as in Example 1, then, a gel patch (product) was prepared by using this base.

Example 5

32.76.parts of distilled water, 1.5 parts of agar, one part of polyvinyl pyrrolidone, 2.5 parts of Carbol, one part of aluminium silicate, one part of hexaglyceryl tristearate (HLB=2.5), and 0.2 part of sorbitol polyglycidyl ether were placed in a mixer; and the resulting mixture was dissolved at about 50° C. to prepare a homogenous dispersion solution. Then added to the dispersion solution were a preliminarily prepared dispersion solution of 10 parts of glycerin, 20 parts of propylene glycol and 5 parts of sodium polyacrylate, 10 parts of distilled water and 3 parts of polyacrylic acid, for mixing under agitation to prepare a homogenous kneaded mixture. Mixed into the kneaded mixture was a solution of 0.04 part of fluocinolone acetonide preliminarily dissolved in 12 parts of crotamiton, to prepare a gel patch base in which fluocinolone acetonide was homogeneously dispersed at dissolution state. In the same manner as in Example 1, then, a gel patch (product) was prepared by using this base.

Example 6

34.95 parts of distilled water, 0.5 part of agar, 2 parts of gelatin, 3 parts of polyvinyl alcohol, one part of aluminium silicate, 1.5 parts of polyoxyethylene (10) hardened castor oil (HLB=6.5) and one part of polypropylene glycol diglycidyl ether were placed in a mixer; and the resulting mixture was dissolved at about 50° C. to prepare a homogenous dispersion solution. Then added to the dispersion solution were a preliminarily prepared dispersion solution of 25 parts of polyethylene glycol and 3 parts of sodium polyacrylate, 10 parts of distilled water, and 3 parts of methoxyethylene maleic anhydride copolymer, for mixing under agitation to prepare a homogenous kneaded mixture. Mixed into the kneaded mixture was a solution of 0.05 part of betametasone valerate preliminarily dissolved in 15 parts of crotamiton, to prepare a gel patch base in which betametasone valerate was homogeneously dispersed at dissolution state. In the same manner as in Example 1, then, a gel patch (product) was prepared by using this base.

Example 7

49.845 parts of distilled water, 9.5 parts of kaolin, 0.25 part of titanium oxide, 0.6 part of sesqui-oleate sorbitan (HLB=4.3), 0.5part of synthetic aluminium silicate, and 0.3 part of tartaric acid were placed in a mixer; and resulting mixture was dissolved at about 50° C. to prepare a homogenous dispersion solution. Then added to the dispersion solution was a preliminarily prepared dispersion solution of 24 parts of glycerin, 9 parts of sodium polyacrylate and 3 parts of carboxymethyl cellulose sodium, for mixing under agitation to prepare a homogenous kneaded mixture. Mixed into the kneaded mixture was a solution of 0.005 part of betametasone valerate preliminarily dissolved in 3 parts of crotamiton, to prepare a gel patch base in which betametasone valerate was homogeneously dispersed at dissolution state. Subsequently, the base was spread on a non-woven fabric (mean air permeability: 190 cm$^3$/cm$^2$/s) so that the amount of the base to be 500 g/m$^2$, using a spreader; additionally, the surface of the base was coated with a polyester film; and then, the resulting non-woven fabric was cut into pieces of a predetermined size, to recover a gel patch (product).

Comparative Example 1
(In case that the amount of crotamiton blended is less than 200-fold that of the steroid)

40.19 parts of distilled water, 5 parts of gelatin, 3 parts of polyvinyl alcohol, 5 parts of kaolin, 0.1 part of monostearate polyethylene glycol (2EO) (HLB=4), 0.2 part of dihydroxyaluminium aminoacetate, and 0.5 part of tartaric acid were placed in a mixer; and the resulting mixture was dissolved at about 50° C., to prepare a homogenous dispersion solution. Added to the dispersion solution was a preliminarily prepared dispersion solution of 40 parts of glycerin and 5 parts of sodium polyacrylate, for mixing under agitation to prepare a homogenous kneaded mixture. Mixed into the kneaded mixture was a solution of 0.01 part of betametasone valerate preliminarily dissolved in one part of crotamiton, to prepare a gel patch base containing betametasone valerate. In the same manner as in Example 1, then, a gel patch (product) was prepared by using this base.

Comparative Example 2
(In case that the ratio of a surfactant blended to crotamiton is less than 1/20)

41.18 parts of distilled water, 3 parts of gelatin, 2.5 parts of polyvinyl alcohol, one part of Carbol, one part of titanium oxide, 0.2 part of monostearate sorbitan (HLB=4.7) and 0.1 part of polyethylene glycol diglycidyl ether were placed in a mixer; and the resulting mixture was dissolved at about 50° C. to prepare a homogenous dispersion solution. Then added to the dispersion solution was a preliminarily prepared dispersion solution of 30 parts of glycerin, 10 parts of polyethylene glycol and 5 parts of sodium carboxymethyl cellulose, for mixing under agitation to prepare a homogenous kneaded mixture. Mixed into the kneaded mixture was mixed a solution of 0.02 part of beclometasone propionate preliminarily dissolved in 6 parts of crotamiton, to prepare a gel patch base containing beclometasone propionate. In the same manner as in Example 1, then, a gel patch (product) was prepared by using this base.

Comparative Example 3
(In case that the ratio of a surfactant blended to crotamiton is more than 1/5)

42.86 parts of distilled water, 3 parts of polyvinyl alcohol, 0.5 part of carboxyvinyl polymer, 6 parts of kaolin, 0.5 part of titanium oxide, 2.5 parts of monolaurate sorbitan (HLB=8.6), 14 parts of sorbitol solution (70%) and 0.3 part of tartaric acid were placed in a mixer; and the resulting mixture was dissolved at about 50° C. to prepare a homogenous dispersion solution. Then added to the dispersion solution was a preliminarily prepared dispersion solution of 15 parts of glycerin, 5 parts of sodium polyacrylate, 0.15 part of magnesiumaluminatemetasilicate, 0.01 part of dry-aluminium hydroxide gel, and 0.15 part of sodium edetate, for mixing under agitation to prepare a homogenous kneaded mixture. Mixed in the kneaded mixture was a solution of 0.03 part of prednisolone acetate valerate preliminarily dissolved in 10 parts of crotamiton, to prepare a gel patch base containing prednisolone acetate valerate. In the same manner as in Example 1, then, a gel patch (product) was prepared by using this base.

Comparative Example 4
(In case that crotamiton is contained at more than 15 wt % in base)

26.76 parts of distilled water, 1.5 parts of agar, one part of polyvinylpyvrolidone, 2.5 parts of Carbol, one part of aluminium silicate, one part of hexaglyceryl tristearate (HLB=2.5) and 0.2 part of sorbitol polyglycidyl ether were placed in a mixer; and the resulting mixture was dissolved at about 50° C., to prepare a homogenous dispersion solution. Then added to the dispersion solution were a preliminarily prepared dispersion solution of 10 parts of glycerin, 20 parts of propylene glycol and 5 parts of sodium polyacrylate, 10 parts of distilled water and 3 parts of polyacrylic acid, for mixing under agitation to prepare a homogenous kneaded mixture. Mixed into the kneaded mixture was a solution of 0.04 part of fluocinolone acetonide preliminarily dissolved in 18 parts of crotamiton, to prepare a gel patch base containing fluocinolone acetonide. In the same manner as in Example 1, then, a gel patch (product) was prepared by using this base.

Comparative Example 5
(In case that crotamiton is contained above 15 wt % in base and the ratio of a surfactant blended to crotamiton is more than 1/5)

29.95 parts of distilled water, 0.5 part of agar, 2 parts of gelatin, 3 parts of polyvinyl alcohol, one part of aluminium silicate, 4.5 parts of polyoxyethylene (10) hardened castor oil (HLB=6.5) and one part of polypropylene glycol diglycidyl ether were placed in a mixer; and the resulting mixture was dissolved at about 50° C., to prepare a homogenous dispersion solution. Then added to the dispersion solution were a preliminarily prepared dispersion solution of 25 parts of polyethylene glycol and 3 parts of sodium polyacrylate, 9 parts of distilled water and 3 parts of methoxyethylene maleic anhydride copolymer, for mixing under agitation to prepare a homogenous kneaded mixture. Mixed into the kneaded mixture was a solution of 0.05 part of betametasone valerate preliminarily dissolved in 18 parts of crotamiton, to prepare a gel patch base containing betametasone valerate. In the same manner as in Example 1, then, a gel patch (product) was prepared by using this base.

Comparative Example 6
(In case that the amount of crotamiton blended is less than 200-fold the amount of the steroid and the HLB of the surfactant is less than 2)

40.19 parts of distilled water, 5 parts of gelatin, 3 parts of polyvinyl alcohol, 5 parts of kaolin, 0.1 part of sorbitan trioleate (HLB=1.7), 0.2 part of dihydroxyaluminium aminoacetate and 0.5 part of tartaric acid were placed in a mixer; and the resulting mixture was dissolved at about 50° C., to prepare a homogenous dispersion solution. Then added to the dispersion solution was a preliminarily prepared dispersion solution of 40 parts of glycerin and 5 parts of sodium polyacrylate, for mixing under agitation to prepare a homogenous kneaded mixture. Mixed into the kneaded mixture was a solution of 0.01 part of prednisolone acetate valerate preliminarily dissolved in one part of crotamiton, to prepare a gel patch base containing prednisolone acetate valerate. In the same manner as in Example 1, then, a gel patch (product) was prepared by using this base.

Comparative Example 7
(In case that the amount of crotamiton blended is less than 200-fold the amount of the steroid and that the HLB of the surfactant is more than 11)

40.19 parts of distilled water, 5 parts of gelatin, 3 parts of polyvinyl alcohol, 0.1 part of monostearate polyethylene glycol (45EO) (HLB=18.0), 5 parts of kaolin, 0.2 part of dihydroxyaluminium aminoacetate and 0.5 part of tartaric acid were placed in a mixer; and the resulting mixture was dissolved at about 50° C., to prepare a homogenous dispersion solution. Then added to the dispersion solution was a preliminarily prepared dispersion solution of 40 parts of glycerin and 5 parts of sodium polyacrylate, for mixing under agitation to prepare a homogenous kneaded mixture. Mixed into the kneaded mixture was a solution of 0.01 part of dexametasone valerate preliminarily dissolved in one part of crotamiton, to prepare a gel patch base containing dexametasone valerate. In the same manner as in Example 1, then, a gel patch (product) was prepared by using this base.

Reference Example 1
(In case that the mean air permeability of a support is more than 200 $cm^3/cm^2/s$)

In the same manner as in Example 1 except for the use of a non-woven fabric with a mean air permeability of 220 $cm^3/cm^2/s$, a gel patch (product) was prepared.

Test Example 1
(Assessment of steroid stability over time)

Gel patches recovered in Examples 1 to 6 and Comparative Examples 1 to 7 were filled and sealed in air-tight aluminium packages at one sheet per package; and the gel patches were stored under conditions of temperatures of 25° C., 40° C., 50° C. and 60° C., respectively, and a relative humidity of 75% for one month. Subsequently, the residual steroid ratio (ratio in % of residual steroid to initial steroid) was determined by high-performance liquid chromatography. The results are shown in Tables 1 and 2.

TABLE 1

| | Residual steroid ratio (%) | | | | | |
|---|---|---|---|---|---|---|
| | Example 1 | Example 2 | Example 3 | Example 4 | Example 5 | Example 6 |
| 25° C.; one month | 99.3 | 99.5 | 99.2 | 98.9 | 98.9 | 99.1 |
| 40° C.; one month | 98.9 | 99.0 | 98.9 | 98.2 | 98.6 | 98.8 |
| 50° C.; one month | 98.6 | 99.1 | 98.4 | 96.8 | 97.9 | 98.0 |
| 60° C.; one month | 98.2 | 98.8 | 97.4 | 95.2 | 96.3 | 97.6 |

TABLE 2

| | Residual steroid ratio (%) | | | | | | |
|---|---|---|---|---|---|---|---|
| | Comparative Example 1 | Comparative Example 2 | Comparative Example 3 | Comparative Example 4 | Comparative Example 5 | Comparative Example 6 | Comparative Example 7 |
| 25° C.; one month | 52.3 | 85.1 | 85.8 | 85.3 | 88.3 | 48.1 | 51.2 |
| 40° C.; one month | 46.8 | 75.4 | 80.2 | 79.6 | 82.7 | 38.8 | 40.1 |

TABLE 2-continued

| | Residual steroid ratio (%) | | | | | | |
|---|---|---|---|---|---|---|---|
| | Comparative Example 1 | Comparative Example 2 | Comparative Example 3 | Comparative Example 4 | Comparative Example 5 | Comparative Example 6 | Comparative Example 7 |
| 50° C.; one month | 40.6 | 68.6 | 76.7 | 71.8 | 80.2 | 31.3 | 33.5 |
| 60° C.; one month | 35.2 | 60.3 | 68.2 | 65.4 | 70.5 | 25.1 | 28.6 |

Test Example 2
(Assessment of stability of physical properties of gel patches over time)

Gel patches recovered in Examples 1 to 6 and Comparative Examples 1 to 7 were filled and sealed in air-tight aluminium packages at one sheet per one package; and the gel patches were stored under conditions of temperatures of 25° C., 40° C., 50° C. and 60° C., respectively, and a relative humidity of 75% for one month. Subsequently, the bleeding of crotamiton onto the base surface (phase separation of crotamiton in plaster) and stickiness of the base (decrease of adhesive force of base) were assessed. The results are shown in Tables 3 to 6. The assessment was done visually and with finger touch, according to the following standards.

Assessment standard of bleeding

None: state with no change observed.

Slight bleeding: state with no deposition found on a peeled coating surface but with a slippery touch on fingers when touching the base surface of gel patches.

Bleeding: state with oily drops deposited on a peeled coating surface.

Assessment standard of stickiness

None: state with no change observed.

Slight stickiness: state with no deposition found on a peeled coating surface but with a part of adhesives deposited on fingers when touching the base surface of gel patches.

Stickiness: state with a part of adhesives deposited on a peeled coating surface.

TABLE 3

| | Presence or absence of crotamiton bleeding from base (phase separation) | | | | | |
|---|---|---|---|---|---|---|
| | Example 1 | Example 2 | Example 3 | Example 4 | Example 5 | Example 6 |
| 25° C.; one month | none | none | none | none | none | none |
| 40° C.; one month | none | none | none | none | none | none |
| 50° C.; one month | none | none | none | none | none | none |
| 60° C.; one month | none | none | none | none | none | none |

TABLE 4

| | Presence or absence of stickiness (decrease of adhesive force) | | | | | |
|---|---|---|---|---|---|---|
| | Example 1 | Example 2 | Example 3 | Example 4 | Example 5 | Example 6 |
| 25° C.; one month | none | none | none | none | none | none |
| 40° C.; one month | none | none | none | none | none | none |
| 50° C.; one month | none | none | none | none | none | none |
| 60° C.; one month | none | none | none | none | none | none |

TABLE 5

| | Presence or absence of crotamiton bleeding from base (phase separation) | | | | | | |
|---|---|---|---|---|---|---|---|
| | Comparative Example 1 | Comparative Example 2 | Comparative Example 3 | Comparative Example 4 | Comparative Example 5 | Comparative Example 6 | Comparative Example 7 |
| 25° C.; one month | None | bleeding | none | bleeding | none | bleeding | slight bleeding |
| 40° C.; one month | None | bleeding | none | bleeding | none | bleeding | slight bleeding |
| 50° C.; one month | None | bleeding | none | bleeding | bleeding | bleeding | bleeding |

TABLE 5-continued

Presence or absence of crotamiton bleeding from base (phase separation)

| | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| 60° C.; one month | None | bleeding | none | bleeding | bleeding | bleeding | bleeding |

TABLE 6

Presence or absence of stickiness (decrease of adhesive force)

| | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| 25° C.; one month | None | None | sticking | None | sticking | sticking | slight sticking |
| 40° C.; one month | None | None | sticking | None | sticking | sticking | slight sticking |
| 50° C.; one month | None | slight sticking | sticking | sticking | sticking | sticking | sticking |
| 60° C.; one month | None | slight sticking | sticking | sticking | sticking | sticking | sticking |

Test Example 3
(Assessment of stability of adhesive force of gel patch over time)

Gel patches recovered in Examples 1 to 6 and Comparative Examples 1 to 7 were filled and sealed in air-tight aluminium packages at one sheet per one package; and the gel patches were stored under conditions of temperatures of 25° C., 40° C., 50° C. and 60° C., respectively, and a relative humidity of 75% for one month. Subsequently, the adhesive force was assessed over time. The adhesive force was measured according to the method described in Nichiban Rolling Ball Method (Adhesion Manual, Polymer Publication, the 14-th 15 edition, p. 381, 1985) as follows. When a 20/32-inch ball (made of stainless steel) was rolled, a rolling distance of the ball was measured as the indicator of the adhesive force. The results are shown in Tables 7 to 8.

TABLE 7

Assessment results of adhesive force of dosage form (mm)

| | Example 1 | Example 2 | Example 3 | Example 4 | Example 5 | Example 6 |
|---|---|---|---|---|---|---|
| 25° C.; one month | 36.2 | 36.0 | 38.2 | 37.9 | 40.9 | 40.1 |
| 40° C.; one month | 34.5 | 35.0 | 33.9 | 31.2 | 33.6 | 32.8 |
| 50° C.; one month | 35.5 | 35.3 | 38.4 | 34.8 | 35.9 | 38.0 |
| 60° C.; one month | 36.3 | 38.8 | 40.4 | 36.2 | 42.3 | 42.6 |

TABLE 8

Assessment results of adhesive force of dosage form (mm)

| | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| 25° C.; one month | 38.0 | 50.1 | 47.8 | 55.7 | 46.2 | 52.1 | 42.2 |
| 40° C.; one month | 32.4 | 56.8 | 49.1 | 58.5 | 50.7 | 55.3 | 40.5 |
| 50° C.; one month | 35.9 | 65.6 | 52.7 | 67.8 | 58.1 | 61.2 | 48.9 |
| 60° C.; one month | 38.4 | 70.6 | 62.3 | 75.4 | 64.5 | 66.8 | 52.1 |

Test Example 4
(Assessment of bleeding of the base onto the support)

Gel patches recovered in Examples 1 and 7 and Reference Example 1 were filled and sealed in air-tight aluminium packages at one sheet per one package; and the gel patches were stored under conditions of temperatures of 25° C., 40° C., 50° C. and 60° C., respectively, and a relative humidity of 75% for one month. Subsequently, the bleeding of the base onto the support was assessed. The results are shown in Table 9. Furthermore, the assessment was carried out visually and by finger touch according to the following standards.

Assessment standard of bleeding

None: state with no change observed.

Slight bleeding: state with no deposition found on a peeled coating surface but with a slippery touch on fingers when touching the base surface of gel patches.

Bleeding: state with oily drops deposited on a peeled coating surface.

TABLE 9

| | Presence or absence of bleeding of base on support | | |
|---|---|---|---|
| | Example 1 | Example 7 | Reference Example 1 |
| 25° C.; one month | None | none | None |
| 40° C.; one month | None | none | None |
| 50° C.; one month | None | none | Bleeding |
| 60° C.; one month | None | none | Bleeding |

Industrial Application

As has been described above, the gel patches of the present invention contain a steroid as an effective ingredient at 0.005 to 0.05 wt %, crotamiton as a stabilizer at an amount of 200- to 3000-fold the weight of the steroid and at less than 15 wt %, and a surfactant at an amount of $\frac{1}{20}$- to $\frac{1}{5}$-fold the amount of crotamiton blended. According to the gel patches of the present invention, the decomposition of the steroid is sufficiently prevented and the adhesive force is stabilized over time despite of the dissolution state. Additionally the occurrence of so-called bleeding due to the phase separation in the base and the occurrence of so-called stickiness due to the decrease of the adhesive force of the base can be prevented. In accordance with the present invention, thus, it can provide steroid-containing gel patches with very excellent stability over time.

According to the process of the present invention, furthermore, the steroid-containing gel patches of the present invention can efficiently be produced in a simple manner, where the steroid is satisfactorily dissolved at a homogeneously dispersed state.

What is claimed is:

1. A steroid-containing gel patch comprising a base which contains a steroid as an effective ingredient at 0.005 to 0.05% by weight, crotamiton as a stabilizer at 15% by weight or less, a crosslinking agent at 0.01 to 5% by weight and a surfactant, wherein the amount of said crotamiton is 200 to 3000-fold the weight of said steroid blended and the amount of said surfactant blended is $\frac{1}{20}$ to $\frac{1}{5}$-fold the weight of said crotamiton blended; and a support which is a non-woven fabric having a mean air permeability of 200 cm$^3$/cm$^2$/s or less.

2. A steroid-containing gel patch according to claim 1, wherein the amount of said crotamiton blended is 13% by weight or less and is 250 to 1500-fold the weight of said steroid blended.

3. A steroid-containing gel patch according to claim 1, wherein the amount of said crotamiton blended is 10% by weight or less and is 300 to 1200-fold the weight of said steroid blended.

4. A steroid-containing gel patch according to claim 1, wherein the amount of said surfactant blended is $\frac{1}{15}$ to $\frac{1}{6}$-fold the weight of said crotarniton blended.

5. A steroid-containing gel patch according to claim 1, wherein the amount of said surfactant blended is $\frac{1}{12}$ to $\frac{1}{8}$-fold the weight of said crotamiton blended.

6. A steroid-containing gel patch according to claim 1, wherein the base further contains a water-soluble polymer at 0.1 to 30% by weight.

7. A steroid-containing gel patch according to claim 1, wherein the base further contains a moisturizer at 10 to 60% by weight.

8. A steroid-containing gel patch according to claim 1, wherein the base further contains water at 20 to 70% by weight.

9. A steroid-containing gel patch according to claim 1, wherein said surfactant is a nonionic surfactant.

10. A steroid-containing gel patch according to claim 1, wherein an HLB value of said surfactant is 2 or more to 11 or less.

11. A steroid-containing gel patch according to claim 1, wherein said steroid is at lease one selected from the group consisting of prednisolone acetate valerate, dexamwetasone valerate, betametasone valerate, flucinolone acetonide and beclometasone propionate.

12. A steroid-containing gel patch according to claim 1, wherein the residual steroid ratio after one-month storage under conditions of a temperature of 60° C. and a relative humidity of 75% is 95% or more.

13. A process for producing a steroid-containing gel patch that comprises:

preparing a solution of a steroid in crotamiton by mixing 0.005 to 0.05 part by weight of the steroid with 15 parts by weight or less of crotamiton wherein the crotamiton is in an amount 200- to 3000-fold the weight of said steroid;

preparing a homogeneously kneaded mixture by mixing together a surfactant in an amount of $\frac{1}{20}$ to $\frac{1}{5}$-fold the weight of said crotamiton, 20 to 70 part by weight of water, 0.1 to 30 part by weight of a water-soluble polymer, 10 to 60 part by weight of a moisturizer and 0.01 to 5 part by weight of a crosslinking agent;

preparing a gel patch base where the steroid is homogeneously dispersed at dissolution state, by adding said solution of the steroid in crotamiton to said kneaded mixture; and spreading the gel patch base on a support which is a non-woven fabric having mean air permeability of 200 cm$^3$/cm$^2$/s or less to produce the gel patch.

* * * * *